Aug. 7, 1956 C. SORIA Plant Pat. 1,505
ROSE PLANT
Filed Sept. 21, 1955
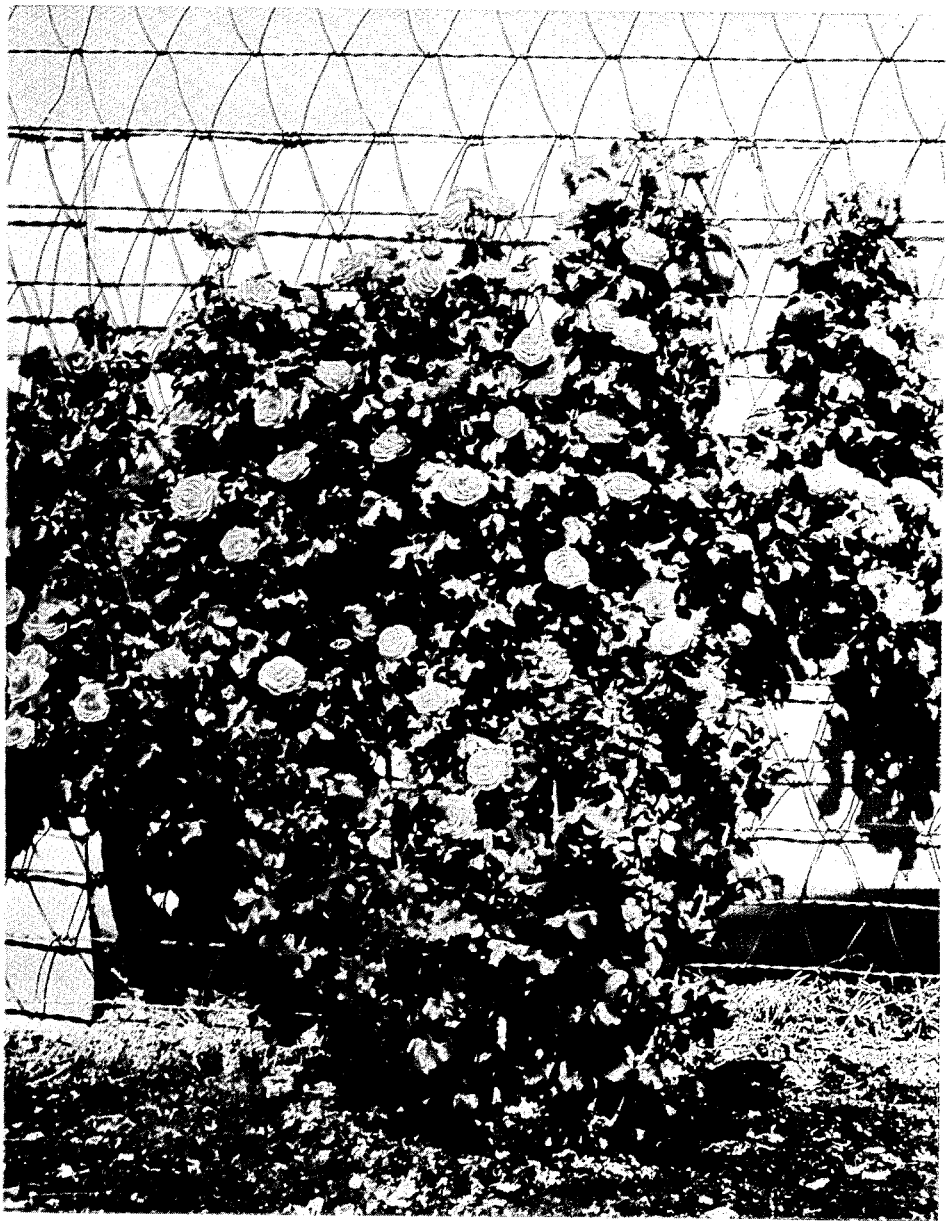
INVENTOR
Cipriano Soria
By Orville M. Kile
Plant Patent Agent United States Patent Office Plant Pat. 1,505
Patented Aug. 7, 1956

1,505

ROSE PLANT

Cipriano Soria, Livermore, Calif., assignor to Germain's, Inc., Los Angeles, Calif.

Application September 21, 1955, Serial No. 535,777

1 Claim. (Cl. 47—61)

My present discovery pertains to an improvement in polyantha rose plants, particular with reference to their climbing qualities. This new variety originated as a cultivated sport of the variety Garnette (unpatented) and was discovered by me in my regular duties at nurseries located at Livermore, California. Because it seemed to have possibilities, I watched it and later asexually reproduced it from buds at the same location. This asexual reproduction has proved the variety's qualities to be permanently fixed.

My new variety's principal difference from its parent is the climbing quality, although it does have some other differences such as its greater vigor of growth, more wiry stems, habit of breaking more freely, etc. It is very prolific in its production of flowers and has been very healthy.

Accompanying illustrations show the vigorous and climbing growth of this new variety, as well as the foliage and flowers in approximately their true colors, except the red should be slightly darker.

Plate numbers in the following detailed description refer to Ridgway's Color Standards and Nomenclature, whereas other color designations refer to the usual dictionary meaning of the term.

THE PLANT

Growth: Vigorous; climbing; breaks freely; attains a height of 8 to 10 feet in a single season, but extends much higher if left untrimmed.

Blooming habit: Prolific producer of bloom throughout the season.

Borne: Singly and in clusters.

Stems:

*Strength.*—Strong and wiry.

*Length.*—Medium.

*Color.*—Approximately Elm Green (Plate XVII).

Foliage:

*Quantity.*—Abundant.

*Leaves.*—Three to seven leaflets, with terminal leaflet much larger.

*Size.*—Terminal leaflet from 2 to 2½ inches long and 1 to 1½ inches wide.

*Shape.*—Elliptical, with rounded base and sharp apex. Edge sharply serrated.

*Texture.*—Leathery. Midrib prominent.

*Color.*—Upper surface dark green, approximately Dark Dull Yellow Green (Plate XXXII) in hue but with considerably more brilliance. Under surface approximately Light Elm Green (Plate XVII).

*Rachis.*—Slender; grooved and usually bronzed on upper surface.

*Stipules.*—Narrow; clinging, but with long, sharp points.

THE FLOWER

Bud:

*Size.*—Small, approximately ¾ to 1 inch long.

*Shape.*—Ovoid.

*Sepals.*—Mostly simple; slightly branched.

*Color.*—Not shown in the color guide used, but falls between Rose Color (Plate XII) and Carmine (Plate I), with a frosty overcast. White aiglet.

Bloom:

*Size.*—Medium, averaging about 2 inches in diameter.

*Form.*—Full, with depressed center at first, opening into cupshape. Petals seldom reflex.

*Color.*—Opening flower has the same frosty appearance as the bud. Inside of the petals—visible in the open flower—is velvety dark red—a color not shown in the color guide but which falls between Rose Red (Plate XII) and Carmine (Plate I). Petals have a white aiglet but this is seldom visible.

*Petalage.*—Approximately 45 to 50 petals.

*Fragrance.*—Slight.

*Longevity.*—Flowers last well on the plant and as cut flowers.

Petals:

*Size.*—Outer petals are ¾ to 1 inch long.

*Shape.*—Obcordate. Edge smooth.

*Appearance.*—Soft and velvety.

*Arrangement.*—Regular.

*Persistence.*—Clinging.

Reproductive organs:

*Pistils.*—Many; tightly bunched in center of flower. *Styles* irregular in length. *Stigmas* light yellow.

*Stamens.*—Few; surround pistils. *Filaments* irregular. *Anthers* very small.

Having thus disclosed my discovery, I claim:

The new and distinct variety of polyantha rose plant, substantially as herein shown and described, characterized particularly by its vigorous, sturdy growth; its climbing habit; its wiry stems; its prolific production of dark red flowers throughout the season; and its habit of breaking freely.

No references cited.